May 6, 1958 F. W. ANDERSON Plant Pat. 1,698

ALMOND TREE

Filed Sept. 16, 1957

WITNESS

Addison E. Avery

INVENTOR

Frederic W. Anderson

Webster & Webster

ATTYS.

United States Patent Office

Plant Pat. 1,698

Patented May 6, 1958

1,698

ALMOND TREE

Frederic W. Anderson, Merced, Calif.

Application September 16, 1957, Serial No. 684,375

1 Claim. (Cl. 47—62)

The present invention relates to a new and distinct variety of almond tree which is characterized—as to novelty—particularly by a late blooming period, and heavy production of commercially acceptable nuts which are so well sealed and firm that the kernels are effectively protected.

It is recognized that most almond varieties bloom in early season; the blooming period of the usual commercial varieties as grown in the State of California nomally extending from late January into March. The blooming thus occurs during a period which is commonly quite cold and wet, especially in the interior valley of California. Because of these adverse weather conditions, reduction in size of the crop from frost and rain damage frequently occurs; rain being a deterrent to effective pollination, and further compelling the use of sprays to control such diseases as brown rot and shot-hole fungus. Also, protection from frost by smudging, heating, or other means is not always effective. In all cases the use of sprays and frost preventive measures is costly.

With respect to the well-known varieties of almonds grown in the State of California, the blooming occurs—generally—in the following order, to-wit: The Jordanola begins to bloom in the latter portion of January; the Ne Plus Ultra and IXL varieties follow about a week later; the Nonpareil, Peerless, and Drake about two weeks later; and the Texas (Mission) about three weeks later.

The Texas is thus the latest of the above varieties to bloom, and the present variety has a blooming period which begins—on the average—a day or two later than the Texas; this being a very advantageous attribute, as there is a substantial avoidance of damage and losses due to earlier, and adverse weather conditions.

The present variety of almond tree was originated by me during a long, extensive, and continuing program seeking improved late blooming varieties which produce commercially acceptable crops; such program being conducted in my experimental almond orchard located near Le Grand, county of Merced, California.

To this end I have annually grown large numbers of seedlings produced from open-pollinated seeds, or from controlled crosses. Records kept by me on such seedlings evidence the fact that the majority thereof bloom early, and all that bloomed before the Texas were discarded. The remaining, late blooming seedlings were allowed to bear, and those that showed commercial promise were top-worked on orchard trees in my experimental orchard, located as aforesaid, and again were observed and checked for blooming period and production; comparison having been made with the common commercially grown varieties heretofore mentioned, and which I also have growing in my said experimental orchard.

The present variety of almond tree is one of such seedlings (both parents unknown or unrecorded), and it has produced excellent crops over several consecutive harvests; the asexual reproductions—by careful comparison—carrying forward all of the characteristics of the parent tree of the variety.

As compared with the Texas, the present variety starts blooming—as aforesaid—very shortly thereafter, and extends a few days longer. Top-worked on the same tree at the same time, this variety bears heavier crops than the Texas; the nuts have a softer shell; and the percentage of kernels averages 53% as compared with 43%. Additionally, the nut of the present variety has a ventral suture line which is only about one-half the width of that of the Texas, and the two varieties are interfertile.

As compared with the Nonpareil, this variety blooms about one week later, although the blooming periods overlap to some extent. The Nonpareil has a larger, flatter, and smoother kernel, while the present variety has a thicker, harder, and better sealed shell, so that insects, worms, birds, moisture, and decay do not cause the damage and losses so common to the Nonpareil. In my experimental orchard the Nonpareil has averaged 63% kernels as compared to 53% for the present variety, and about 26 kernels to the ounce as compared to 28 kernels to the ounce for this variety. Here too the two varieties are interfertile.

Figure 2:
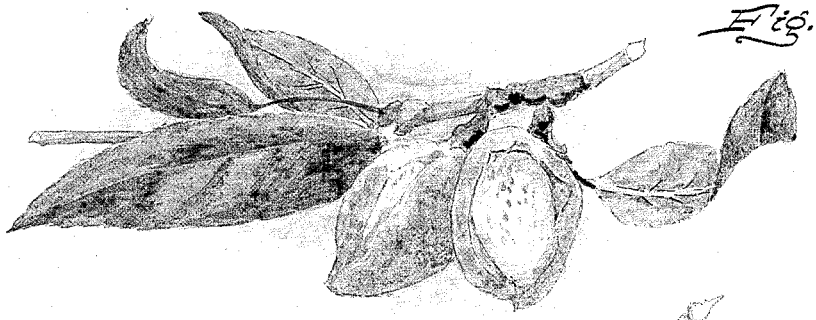
Fig. 2 is a similar but fragmentary view; one of the hulls being shown substantially fully open.
Figure 1:
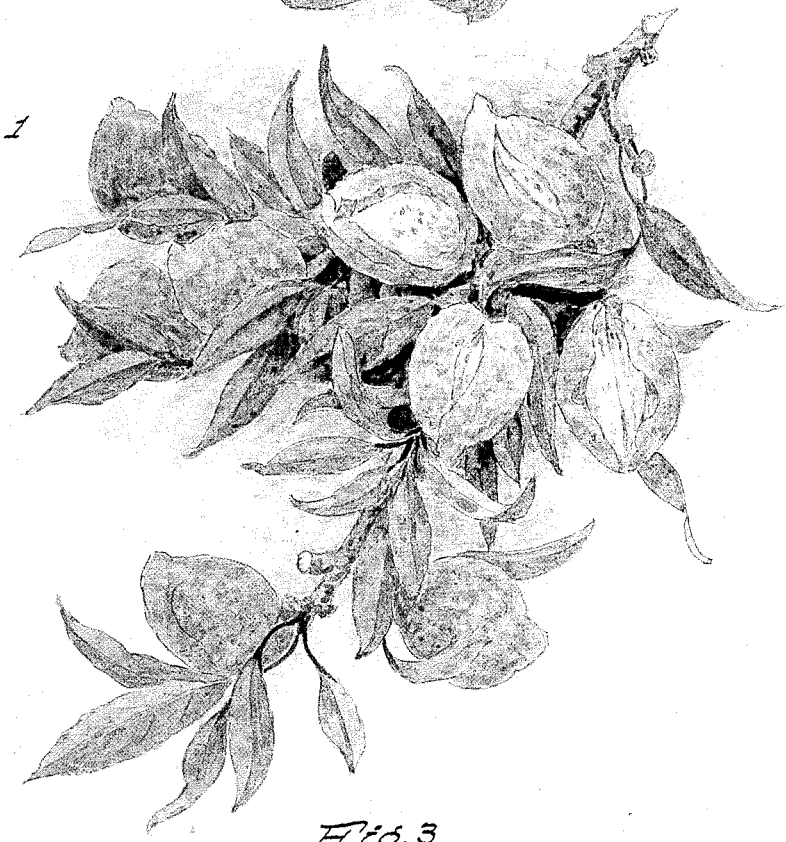
Fig. 1 is an elevation of a twig with leaves and ripe nuts of the variety; a number of the hulls being shown partially open.
Figure 4:
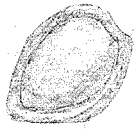
Fig. 4 is a view of a kernel as remaining in one-half of its shell.
Figure 3:
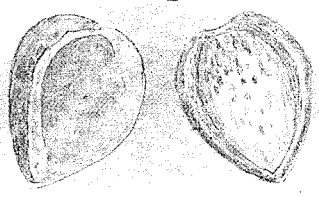
Fig. 3 is a view of one of the nuts with the hull separated into halves; the shell remaining in one of such halves and being exposed.
Figure 5:
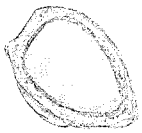
Fig. 5 is a similar view, but with the skin removed from the exposed portion of the kernel.

Referring now specifically to the botanical details of this new and distinct variety of almond tree, the following is an outline description thereof; all major plate identifications being by reference to Maerz and Paul Dictionary of Color:

Tree:

*Density.*—Open.

*Size.*—Medium.

*Vigor.*—Medium.

*Branching habit.*—Medium.

*Foliage.*—Abundant. Leaves: size—blade averages 3″ in length by ¾″ in width; petiole averages ½″ in length; shape—narrow, ovate; margin—crenate; color—larger leaves: top side—medium green (22–L–8), under side—lighter green (21–J–7); smaller leaves: top side—medium green (22–L–6), under side—medium green (22–I–6). Bloom: amount of bloom—average to heavy; color—white; blooming period—begins on the average within a day or two after the Texas. Susceptibility or resistance to insects and diseases—no unusual susceptibility, and occurrences controlled by usual spray practices.

Crop:

*Productivity.*—Heavy.

*Distribution of nuts on tree.*—Well distributed.

*Ripening period.*—Approximately with the Texas.

*Tenacity.*—Hangs on tree well; easy to harvest; hulls and shells readily, with little breakage of kernels.

Hull: Rough; irregular; thin; tough.

*Suture.*—Flat.

*Color.*—Light green (20–E–2), shading to a dull gray (38–A–1 to 39–A–2); without a silvery sheen.

*Dehiscence.*—Opening freely.

*Splitting.*—Along suture; freely at base.

Nut:

*Size.*—Average length, 1⅛". Average width, ¾". Average thickness, 9/16". Average weight—225 nuts to the pound.

*Form.* — Length/width—3/2—ovate. Width/thickness—2/1—plump to medium.

*Shell.*—Soft; medium thickness; smooth.

*Outer shell.*—Hard.

*Inner shell.*—Hard; well sealed.

*Color.*—Medium light (10–F–5).

*Pits.*—Medium size; medium number; medium depth; round; irregular.

*Base.*—Square to gentle slope dorsally. Stem scar—medium.

*Apex.*—Acute; sharp.

*Wing.*—Narrow.

*Inner surface.*—Light.

*Ventral streak.*—Broad to narrow; long; point acute; about half the width of the ventral streak of the Texas.

*Percentage of kernel to nut.*—50% to 55%—average about 53%.

Kernel:

*Size.*—Average length, 13/16". Average width, ½". Average thickness, 5/16". Average weight—28 to the ounce.

*Form.*—Length/width—1.6/1—ovate. Width/thickness—1.6/1—medium.

*Base.*—Square to gently dorsally oblique. Stem scar—small; obtuse.

*Apex.*—Acute; sharp.

*Plumpness.*—Smooth to wrinkled.

*Pellicle.*—Thin.

*Pubescence.*—Medium.

*Color of skin.*—Light golden brown (11–1–8).

*Color of flesh.*—White, with ivory tint (9–A–1).

*Number of doubles.*—Few.

*Defective kernels.*—Very few defectives of any kind.

*Flavor.*—Normal.

*Quality.*—Good.

The tree and its nuts herein described may vary in slight detail due to climatic and soil conditions under which the variety may be grown.

The previously existing varieties of almonds, heretofore mentioned in this specification, are unpatented.

The following is claimed:

A new and distinct variety of almond tree, as described, which is characterized by a late blooming period and heavy production of nuts which are firm and well sealed; additionally characterized—in comparison with the Texas almond—by a blooming period which begins a day or two later and extends a few days longer, shells which are softer, kernels which average 53% as compared with 43% for like grown specimens of the Texas almond, and a ventral suture line which is only about one-half the width; further characterized—in comparison with the Nonpareil almond—by a blooming period which begins about one week later, shells which are thicker, harder, and much better sealed, and kernels which average 53% as compared with 63% for like grown specimens of the Nonpareil almond, the kernels of the latter being larger, flatter, and smoother; and still further characterized by interfertility with both the Texas and Nonpareil almonds.

No references cited.